United States Patent
Chodorge et al.

[11] Patent Number: 6,075,173
[45] Date of Patent: *Jun. 13, 2000

[54] PROCESS FOR PRODUCTION OF ISOBUTENE AND PROPYLENE FROM HYDROCARBON CUTS CONTAINING FOUR CARBON ATOMS

[75] Inventors: Jean Alain Chodorge, Antony; Dominique Commereuc, Meudon; Jean Cosyns, Maule, all of France

[73] Assignee: Institut Francais du Petrole, France

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/958,909

[22] Filed: Oct. 28, 1997

[30] Foreign Application Priority Data

Oct. 28, 1996 [FR] France .................................. 96 13298

[51] Int. Cl.[7] .............................. C07C 1/00; C07C 5/03; C07C 6/00; C10B 57/02

[52] U.S. Cl. ........................ 585/324; 585/326; 585/329; 585/259; 585/262; 585/261; 585/277; 585/518; 585/643; 585/644; 585/647; 585/670; 208/49; 208/57

[58] Field of Search ..................................... 585/324, 326, 585/329, 330, 253, 256, 259, 262, 261, 277, 518, 643, 644, 467, 668, 670; 208/49, 57

[56] References Cited

U.S. PATENT DOCUMENTS

| | | | |
|---|---|---|---|
| 3,728,414 | 4/1973 | Helden et al. | 260/683 D |
| 3,764,633 | 10/1973 | Garner et al. | 260/683.2 |
| 4,132,745 | 1/1979 | Amigues et al. | 260/683.2 |
| 4,287,378 | 9/1981 | Pennella et al. | 585/643 |
| 4,324,938 | 4/1982 | Cosyns et al. | 585/332 |
| 4,558,170 | 12/1985 | Chen et al. | 585/532 |
| 5,120,894 | 6/1992 | McCauley | 585/664 |
| 5,414,179 | 5/1995 | Hunt et al. | 585/519 |
| 5,449,852 | 9/1995 | Chauvin et al. | 585/647 |
| 5,523,502 | 6/1996 | Rubin | 585/324 |

FOREIGN PATENT DOCUMENTS

| | | |
|---|---|---|
| 735727 | 1/1970 | Belgium . |
| 930382 | 7/1973 | Canada . |
| 0 639 549 | 2/1995 | European Pat. Off. . |
| 1493983 | 12/1967 | France . |
| 72013251 | 12/1967 | Japan . |
| 1110826 | 4/1968 | United Kingdom . |

Primary Examiner—Walter D. Griffin
Assistant Examiner—Thuan D. Dang
Attorney, Agent, or Firm—Millen, White, Zelano & Branigan P.C.

[57] ABSTRACT

The present invention concerns a process for the production of isobutene and propylene by metathesis of an olefinic $C_4$ cut. The process comprises three successive steps: 1) selective hydrogenation of butadiene with isomerisation of butene-1 to butene-2; 2) separation by distillation to produce isobutene overhead, leaving a butene-2 bottom cut; 3) metathesis of the butene-2 cut with ethylene. The advantage of this process is that polymerisation quality propylene can be produced very selectively, in contrast to other processes such as dehydrogenation of propane or other cracking processes.

14 Claims, 1 Drawing Sheet

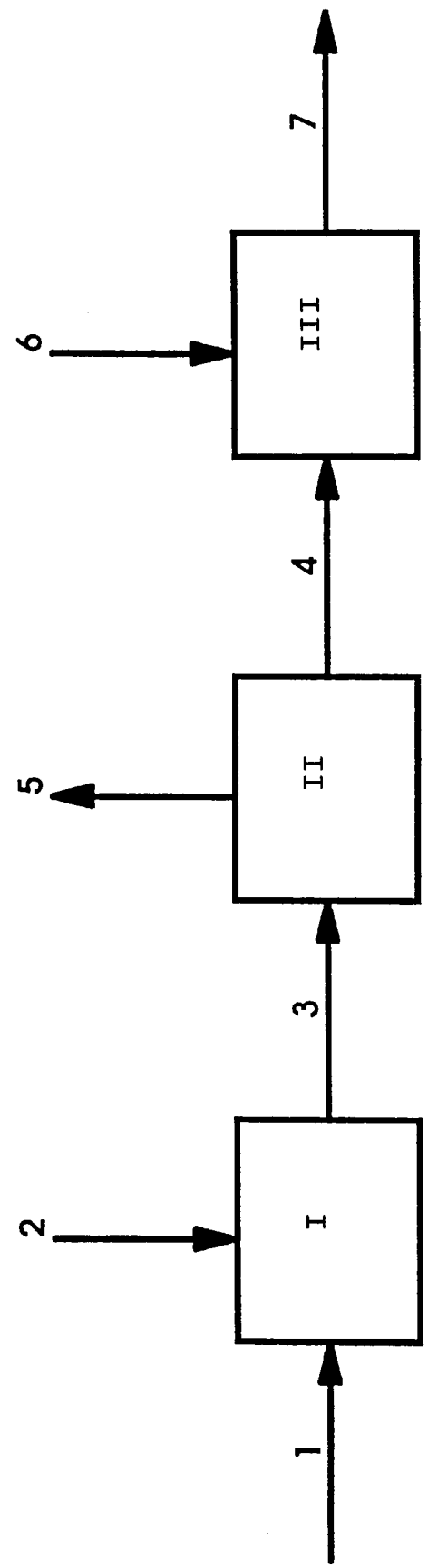
FIGURE

PROCESS FOR PRODUCTION OF ISOBUTENE AND PROPYLENE FROM HYDROCARBON CUTS CONTAINING FOUR CARBON ATOMS

CROSS REFERENCE TO RELATED APPLICATION

This application is related to commonly assigned application Ser. No. 08/644,159 filed May 10, 1996, now U.S. Pat. No. 5,877,365, by Chodorge, Commereuc, Cosyns, Duee, and Torck, said related application being incorporated by reference herein.

BACKGROUND OF THE INVENTION

The invention concerns a process for the production of isobutene and propylene from a $C_4$ cut.

Steam cracking feeds constituted by light paraffinic cuts produces ethylene and propylene which are required for petrochemistry. It also produces a certain number of other heavier products, in particular a $C_4$ hydrocarbon cut which principally contains 1,3-butadiene, isobutene, n-butenes and butanes, accompanied by traces of acetylenic hydrocarbons.

In addition to gasoline and gas oil as the principal products, catalytic cracking of heavy hydrocarbon feeds produces lighter products, among them a $C_4$ hydrocarbon cut which contains principally isobutane, isobutene, n-butenes and butanes, accompanied by small quantities of 1,3-butadiene and acetylenic hydrocarbons.

Until recently, only 1,3-butadiene and isobutene were of use in the polymer industry, in particular the tire industry for the former. An increase in the longevity of tires and a relative stagnation in demand have meant that there is now a surplus of butadiene which is not used or is not used properly. In contrast, there has been a reawakening in interest in isobutene which can be used, for example, for the synthesis of ethers for use as additives in automobile fuels or as a monomer for the synthesis of polyisobutene.

BRIEF SUMMARY OF THE INVENTION

The present invention proposes a process for the treatment of a $C_4$ hydrocarbon cut containing principally isobutene, n-butenes, butanes, and 1,3-butadiene in various quantities, which includes separating the isobutene by distillation and which can transform the 1,3-butadiene and n-butenes to propylene which can, for example, be used for polymerisation.

The relative proportions of ethylene and propylene produced in a steam cracking operation can be modulated to a certain extent by changing the nature of the feed and modifying the operating conditions (severity) of cracking. However, an operative mode which is oriented towards producing a larger proportion of propylene inevitably entrains a reduction in the ethylene yield and higher production of the $C_4$ cut and gasoline fraction.

A further aim of the present invention is to increase the production of propylene while maintaining a high yield of ethylene by treating the $C_4$ hydrocarbon cut and thus without the need for a reduction in the severity of the steam cracker.

BRIEF DESCRIPTION OF THE SEVERAL VIEWS OF THE DRAWING(S)

The FIGURE is a schematic diagram of one embodiment of the invention. A $C_4$ hydrocarbon cut (line 1) enters zone I for hydrogenation and isomerisation in the presence of hydrogen supplied via line 2. The product of zone I enters zone II for distillation via line 3. The distillation process of zone II results in a fraction containing isobutene and the majority of the butene 1 (line 5) and a butene-2 fraction containing the butene-2, a small quantity of butene-1, and n-butane (line 4). The butene-2 fraction from zone II (line 4) enters zone III for metathesis with ethylene (line 6) to produce propylene (line 7).

DETAILED DESCRIPTION OF THE INVENTION

More precisely, the process of the invention is a process for the conversion of an olefinic $C_4$ cut to isobutene and propylene, the cut containing diolefins, butene-1, butene-2, isobutene and acetylenic impurities, the process comprising the following successive steps:

1) selective hydrogenation of diolefins and acetylenic impurities with isomerisation of butene-1 to butene-2 to obtain an effluent containing mainly butene-2 and isobutene, and containing practically no diolefins or acetylenic compounds, preferably by passing the cut in a liquid phase over a catalyst comprising at least one metal selected from the group formed by nickel, palladium and platinum, deposited on a support, at a temperature of 20–200° C., a pressure of 0.1–5 MPa, a space velocity of 0.5–10 $h^{-1}$, and with an $H_2$/diolefin (molar) ratio of 0.5 to 5, preferably 1 to 3;
2) separating, by distillation, an overhead cut containing mainly isobutene and butene-1 which was not converted during the first step, and a bottom cut containing essentially butene-2 and butane, at most 1% by weight of isobutene and at most 1% by weight of butene-1;
3) carrying out metathesis of the butene-2 cut from the preceding step with ethylene, in the presence of a catalyst comprising at least one rhenium oxide deposited on a support, at a temperature in the range 0° C. to 100° C., and at a pressure which is at least equal to the vapour tension of the reaction mixture at the reaction temperature, to obtain an effluent containing propylene, metathesis being followed by separation of the propylene.

The process of the invention will now be described in more detail using the scheme shown in the FIGURE using a $C_4$ hydrocarbon cut entering via a line 1, which contains principally isobutene, n-butenes, butanes, also varying amounts of butadiene. The $C_4$ cut is subjected to a succession of treatments carried out in the following steps, to produce isobutene and propylene:

selective hydrogenation of acetylenic hydrocarbons and butadiene with isomerisation of butene-1 to butene-2;

separation of the isobutene and butene-1 from the butene-2;

metathesis of butene-2 in the presence of ethylene (ethenolysis) producing propylene.

The succession of treatments in the process of the invention has a number of advantages. The most reactive compounds in the cut, namely 1,3-butadiene, for example, which is in varying amounts, also traces of acetylenic hydrocarbons, are transformed in the first step, and will thus not cause side reactions in the following steps. Further, selective hydrogenation of the diolefins (1,3-butadiene and 1,2-butadiene) to butenes and hydroisomerisation of butene-1 can considerably increase the concentration of butene-2 in the cut, which results in an even higher yield of propylene in the metathesis step.

Fractionation of the cut from the hydroisomerisation step, to isobutene and butene-1 and to butene-2, allows the isobutene to be upgraded in various ways without introducing pollutants into the fraction containing the butene-2 which then undergoes metathesis. It also means that a metathesis catalyst with a low or practically zero isomerising action can be used. Further, if, for example, isobutene is transformed into methyl-tertiobutylether by reaction with methanol, the butene-2 will not be contaminated by oxygen-containing by-products as is normal when this reaction is carried out directly on the hydroisomerised cut. The same is true when isobutene is transformed by polymerisation, a preferred route to upgrading isobutene.

Further, in the subsequent metathesis step, the low butene-1 content in the fraction which is rich in butene-2 can produce a propylene selectivity of close to 100%. Butene-1 will react with butene-2 to produce propylene and pentenes and it will react with itself to produce hexenes. Pentenes and hexenes are low value by-products which must be removed in an expensive process. Thus the process can appreciably increase the propylene yield, and facilitates recycling of butene-2 to the metathesis reaction as there are few pentenes and hexenes to be eliminated.

The invention also concerns a facility (shown in the FIGURE) for carrying out the process described above and which comprises, in succession:

a zone 1 for selective hydrogenation with isomerisation of butene-1 to butene-2, said zone comprising at least one means 1 for introducing a cut to be converted, at least one means 3 for removing effluent and at least one means 2 for introducing hydrogen, said zone also comprising at least one bed of a catalyst which preferably comprises at least one metal selected from the group formed by nickel, palladium and platinum, deposited on a support;

a separation zone 2, comprising at least one means 3 for introducing effluent from zone 1, at least one means 5 for removing isobutene and butene-1, and at least one means 4 for removing butene-2 and n-butane;

a metathesis zone 3 containing at least one catalyst, preferably based on a rhenium oxide deposited on a support, and comprising at least one means 4 for introducing effluent from zone 2, at least one means 6 for introducing ethylene and at least one means 7 for removing propylene.

More particularly, the $C_4$ cut originates from an upstream steam cracking zone, the means for introducing the cut to be converted into zone 1 being connected to the steam cracking zone, and the means for introducing ethylene into zone 4 is connected to the steam cracking zone.

The invention will now be described with reference to the FIGURE.

The principal aim of the first step is to transform butadiene and n-butenes to butene-2. The butene-2 is the source of the propylene which is produced in the last metathesis step in the presence of ethylene. It is thus desirable to maximise the yield of butene-2, i.e., to come as close as possible to the thermodynamic proportions. The second aim of this step is to eliminate traces of acetylenic hydrocarbons which are always present in these cuts and which poison or pollute the subsequent steps.

In the first step (zone 1), the following reactions are carried out simultaneously in the presence of hydrogen supplied via line 2:

selective hydrogenation of butadiene to a mixture of n-butenes at thermodynamic equilibrium;

isomerisation of butene-1 to butene-2, to obtain a distribution which is close to thermodynamic equilibrium;

selective hydrogenation of the trace acetylenic hydrocarbons to butenes.

These reactions can be carried out using various specific catalysts comprising one or more metals, for example from group 10 of the periodic table (Ni, Pd, Pt), deposited on a support. A catalyst comprising at least one palladium compound fixed on a refractory mineral support, for example alumina, is preferably used. The quantity of palladium on the support can be in the range 0.01% to 5% by weight, preferably in the range 0.05% to 1% by weight. A variety of pretreatment methods which are known to the skilled person can be applied to improve the selectivity for the hydrogenation of butadiene to butenes to the detriment of complete hydrogenation to butane which must be avoided. The catalyst preferably contains 0.05% to 10% by weight of sulphur. A catalyst constituted by palladium deposited on alumina, and with sulphur, is preferably used.

The catalyst can advantageously be carried out using the process described in French patent FR-93/09529, i.e., before charging it into the hydrogenation reactor, the catalyst is treated with at least one sulphur-containing compound diluted in a solvent, then the catalyst obtained containing 0.05% to 10% (by weight) of sulphur is charged into the reactor and activated in a neutral or reducing atmosphere at a temperature which is in the range 20° C. to 300° C., a pressure which is in the range 0.1 MPa to 5 MPa and a HSV which is in the range 50 $h^{-1}$ to 600 $h^{-1}$, and the feed is brought into contact with this activated catalyst.

The mode of using the catalyst, preferably a palladium catalyst, is not critical, but in general it is preferable to use at least one reactor in downflow mode passing through a fixed bed of catalyst. When the proportion of butadiene in the cut is high, as is the case, for example, with a steam cracking cut when butadiene is not to be extracted for specific uses, it may be of advantage to carry out the transformation in two reactors in series to better control the selectivity towards hydrogenation. The second reactor can be an upflow reactor and may act as a finishing reactor.

The quantity of hydrogen required for all of the reactions carried out in this step is adjusted as a function of the composition of the cut, so that advantageously the hydrogen is only in a slight excess with respect to the theoretical stoichiometry.

The operating conditions are selected so that the reactants and products are in the liquid phase. However, it may be advantageous to select an operating mode such that the products are partially vaporised at the reactor outlet, to facilitate thermal control of the reaction. The temperature can be between 20° C. and 200° C., preferably 50° C. to 150° C., more preferably 60° C. to 100° C. The pressure can be adjusted to between 0.1 MPa and 5 MPa, preferably between 0.5 MPa and 4 MPa and advantageously between 0.5 MPa and 3 MPa. so that the reactants are at least partly in the liquid phase. The space velocity can be in the range 0.5 $h^{-1}$ to 20 $h^{-1}$, preferably in the range 1 $h^{-1}$ to 10 $h^{-1}$, with an $H_2$/diolefins (molar) ratio of 0.5 to 5, preferably 1 to 3.

The hydroisomerisation reactor(s) can advantageously be followed by a stabilisation column which eliminates traces of gaseous hydrocarbons which may be present in the hydrogen supplied.

The aim of the second step (zone 2) is to separate, by distillation, the $C_4$ cut from the preceding step, supplied via line a 3 to obtain a fraction containing isobutene and the majority of the butene-1, and a fraction containing a small quantity of butene-1, the butene-2 and n-butane. This now concentrated isobutene, recovered via line 5, can be used in various fashions. The butene-2 fraction is directed via a line 4 to the metathesis step.

The butene-2 fraction at the bottom of the distillation zone contains at most 1%, preferably at most 0.5% by weight of butene-1, and at most 1% and advantageously at most 0.5% by weight of isobutene. Further, the overhead loss of butene-2 is advantageously maintained at at most 3% by weight with respect to the butene-2 entering the column. An optimised distillation column operates with 90–120 plates and a reflux/feed ratio of 3–5.

The butene-2 fraction from the preceding step contains no external pollutant (for example oxygen-containing pollutants from an etherification step) and can thus be sent directly to a third step of the process (zone 3). In this last step, butene-2 is reacted with ethylene supplied via a line 6, to give propylene by metathesis (leaving via a line 7). Because of the low quantity of butene-1 and isobutene in the feed, by-product formation is very low.

The metathesis of ethylene with butene-2 can be catalysed by a variety of metal oxides deposited on supports. A catalyst comprising at least one rhenium oxide deposited on a support composed of a refractory oxide containing at least alumina, and with an acid nature, is preferably used, for example alumina itself, silica-aluminas or zeolites.

Preferred examples are catalysts comprising rhenium heptoxide deposited on a gamma alumina analogous to that used in reforming catalysts, as described in U.S. Pat. No. 4,795,734. The rhenium content (expressed as rhenium metal) can be in the range 0.01% to 20%, preferably in the range 1% to 15% by weight. The catalysts undergo final thermal activation, for example at a temperature which is in the range 400° C. to 1000° C. for a period of 10 minutes to 5 hours in a non-reducing atmosphere.

Catalysts comprising rhenium heptoxide deposited on an alumina can also be modified by addition of an oxide of another metal. As an example, such modified catalysts comprise rhenium as an oxide, 0.01% to 20% by weight expressed as metallic rhenium, deposited on a support containing at least 75% by weight of alumina and 0.01% to 30% by weight of at least one oxide of a metal selected from the group formed by niobium and tantalum, as described in French patent FR-A-2 709 125.

The metathesis reaction is preferably carried out in the liquid phase, in the absence of oxygen, oxygen-containing compounds and moisture, and at a temperature which is in the range 0° C. to 200° C., preferably in the range 20° C. to 150° C., at a pressure which is at least equal to the vapour tension of the reaction mixture at the reaction temperature.

The catalyst can be used in a fixed bed. However, as it must be regenerated frequently, at least two reactors disposed in parallel must be used, one being in operation while the other is in regeneration mode. A moving catalytic bed is preferably used, such as that described in French patent FR-A-2 608 595. The catalyst is extracted at regular intervals from the bottom of the reactor and continuously transferred to a regeneration system from which it is returned to the top of the reactor.

Because of the limitations imposed by the thermodynamics, unconverted ethylene is fractionated in a first distillation column and recycled to the metathesis reactor. A second distillation column separates propylene and unconverted $C_4$ hydrocarbons which can be recycled to the metathesis reactor. The fractionation scheme is thus more simple than if a large quantity of butene-1 had been present in the feed, as it would have produced more pentenes and hexenes which would have had to have been eliminated before recycling the butenes.

When the process is applied to a $C_4$ steam cracking cut, it may be of advantage to integrate the metathesis unit with the cracker, to take advantage of the fractionation chain of the latter.

The following example illustrates the invention without limiting its scope.

EXAMPLE 1

A $C_4$ cut leaving a steam cracker had the composition shown in Table 1 (stream 1). Abbreviations used in the table are: MAPD=methylacetylene+propadiene, BBV=1,2-butadiene+1-butyne+vinylacetylene.

This $C_4$ cut first underwent hydrogenation and hydroisomerisation. It was continuously introduced, with the mass flow rate shown in Table 1 and at a pressure of 2 MPa, into a first reactor comprising a fixed bed of 2.6 T of a catalyst constituted by palladium on alumina which had first been sulphurised. Hydrogen (mixed with methane) was also injected into this reactor, as shown in Table 1 (stream 2). The effluent from this first reactor was then treated in a finishing reactor charged with 2.5 T of the same catalyst. At the outlet (Table 1, stream 3), the cut was free of acetylenic compounds and the butadiene had essentially been transformed into butenes, which were mainly butene-2s, the butene-1 having been isomerised. The cut was then treated in a stabilisation column where residual hydrogen and methane were separated. After this treatment, the cut had the composition of stream 4 (Table 1).

TABLE 1

| Stream n° (Example 1) (kg/h) | 1 $C_4$ feed | 2 Feed Hydro-isomerisation | 3 Outlet Hydro-isomerisation | 4 $C_4$ outlet Stabilisation | 5 Column head Isobutene | 6 Column bottom Isobutene | 7 Inlet Metathesis | 8 Outlet Metathesis |
|---|---|---|---|---|---|---|---|---|
| (C3 + C3 =) | 10 | 10 | 41 | | | | | |
| MAPD | 31 | 31 | | | | | | |
| Isobutane | 446 | 446 | 446 | 434 | 434 | | | |
| n-Butane | 545 | 545 | 988 | 981 | | 981 | 981 | 981 |
| Isobutene | 5741 | 5741 | 5741 | 5667 | 5575 | 92 | 92 | 46 |
| butene-1 | 3407 | 3407 | 1003 | 951 | 911 | 40 | 40 | 20 |
| Butene-2s | 2250 | 2250 | 12737 | 12686 | 386 | 12300 | 12300 | 1230 |
| 1,3-Butadiene | 8095 | 8095 | | | | | | |
| BBV | 104 | 104 | | | | | | |
| Hydrogen | | 343 | 16 | | | | | |
| Methane | | 197 | 197 | | | | | |
| Ethylene | | | | | | | 5590 | 56 |

TABLE 1-continued

| Stream n° (Example 1) (kg/h) | 1 C₄ feed | 2 Feed Hydro-isomerisation | 3 Outlet Hydro-isomerisation | 4 C₄ outlet Stabilisation | 5 Column head Isobutene | 6 Column bottom Isobutene | 7 Inlet Metathesis | 8 Outlet Metathesis |
|---|---|---|---|---|---|---|---|---|
| Propylene |  |  |  |  |  |  |  | 16520 |
| Pentenes + |  |  |  |  |  |  |  | 150 |
| Total | 20629 | 21169 | 21169 | 20719 | 7306 | 13413 | 19003 | 19003 |

In the second step, the hydroisomerised C₄ cut underwent fractionation in a distillation column. This column comprised about 90 plates and operated at a pressure of 0.7 MPa in the reflux drum, to allow the use of cooling water in the overhead condenser. The reflux ratio was adjusted to limit the loss of butene-2 in the distillate to about 3% and to reduce the butene-1 and isobutene contents in the bottom product to 0.3% and 0.7% respectively, to limit to a maximum the formation of by-product pentenes and hexenes in the subsequent metathesis step.

In the third step, the bottom fraction from the distillation step which contained mainly butene-2 was reacted with ethylene (overall composition: stream 7 in Table 1) over a metathesis catalyst constituted by rhenium oxide on gamma alumina (8% by weight of rhenium metal), prepared as described in U.S. Pat. No. 4,795,734. The C₄ cut was mixed with ethylene supplied to the inlet to the metathesis reactor and with the recycled ethylene and butene streams. The reactor was a moving bed reactor as described in FR-A-2 608 595, at a temperature of 35° C. and at a pressure of 3.5 MPa, and it was coupled with a regenerator operating at 550° C. at atmospheric pressure. The catalyst was extracted from the bottom of the reactor at regular intervals and transferred to the regenerator from which it was returned to the top of the reactor, transfers being made through buffer traps. At the reactor outlet, unconverted ethylene was fractionated in a first distillation column and recycled. A second distillation column separated the propylene and unconverted C₄ hydrocarbons which were also recycled. The composition of the metathesis effluent is shown in Table 1, stream 8.

The overall balance of the transformation was as follows. For 100 parts by weight (pw) of C₄ cut leaving the steam cracker, 1.6 pw of hydrogen and 28 pw of ethylene were consumed, and 27 pw of isobutene and 83 pw of propylene were produced. For the steam cracker from which the treated C₄ cut issues, this balance represented a low ethylene consumption which resulted in a supplemental high production of propylene without having to modify the operating conditions of the cracker.

The advantage of this process is thus the highly selective production of a polymerisation quality propylene due to metathesis of a butene-2 feed containing only small amounts of butene-1 and isobutene, the feed having been obtained by isomerisation and fractionation of a C₄ cut.

We claim:

1. A process for the conversion of an olefinic C₄ cut to isobutene and propylene, the cut containing diolefins, butene-1, butene-2, isobutene and acetylenic impurities, characterized in that said process comprises the following successive steps:
    1) selective hydrogenation of diolefins and acetylenic impurities and simultaneous isomerisation of butene-1 to butene-2, wherein hydrogenation and isomerization occur in the same zone, to obtain an effluent containing mainly butene-2 and isobutene, and containing practically no diolefins or acetylenic compounds;
    2) separating the effluent of step 1, by distillation, an overhead cut containing mainly isobutene and butene-1 which was not converted during the first step, and a bottom cut containing essentially butene-2 and butane, at most 1% by weight of isobutene and at most 1% by weight of butene-1;
    3) metathesis of the butene-2 in the bottom cut from the preceding step with ethylene, in the presence of a catalyst comprising at least one rhenium oxide deposited on a support, at a temperature in the range 0° C. to 100° C., and at a pressure which is at least equal to the vapour pressure of the reaction mixture at the reaction temperature, to obtain an effluent containing propylene, metathesis being followed by separation of the propylene.

2. A process according to claim 1, characterized in that step 1 is carried out by passing said olefinic C₄ cut in the liquid phase over a catalyst comprising at least one metal selected from the group formed by nickel, palladium and platinum, deposited on a support, at a temperature of 20–200° C., a pressure of 0.1–5 MPa, a space velocity of 0.5–10 h⁻¹, with an $H_2$/diolefin (molar) ratio of 0.5 to 5.

3. A process according to claim 2, characterized in that the catalyst of step 1 contains 0.05% to 10% by weight of sulphur.

4. A process according to claim 2, wherein the catalyst of step 1 is treated with at least one sulphur-containing compound diluted in a solvent, then the catalyst obtained containing 0.05% to 10% (by weight) of sulphur is charged into a reactor and activated in a neutral or reducing atmosphere at a temperature which is in the range 20° C. to 300° C., a pressure which is in the range 0.1 MPa to 5 MPa and a HSV which is in the range 50 h⁻¹ to 600 h⁻¹, then the olefinic C₄ cut is brought into contact with said activated catalyst.

5. A process according to any one of claim 2, characterized in that the catalyst of step 1 is constituted by palladium deposited on alumina, and sulphur.

6. A process according to any one of claim 1, characterized in that metathesis is carried out in a moving bed.

7. A process according to claim 1, characterized in that the overhead cut from step 2 contains at most 3% by weight of butene-2.

8. A process according to claim 1, characterized in that the overhead cut undergoes isobutene polymerisation.

9. A process according to claim 1,
    wherein the catalyst of step 3 further comprises niobium oxide or tantalum oxide deposited on the support, wherein 0.01% to 30% by weight of the catalyst is niobium metal or tantalum metal, and
    wherein 0.01% to 20% by weight of the catalyst of step 3 is metallic rhenium, and wherein at least 75% by weight of the support of the catalyst of step 3 is alumina.

10. A process according to claim 1, wherein the $C_4$ cut is derived from a steam cracking process.

11. A process according to claim 1, wherein the $C_4$ cut is derived from a catalytic cracking process.

12. A process according to claim 1, wherein the effluent of the metathesis step is fractionated by a process consisting essentially of the following steps:

a separation step to remove ethylene from said effluent;

a separation to remove propylene from said effluent;

recycling of remaining effluent with the $C_4$ cut in step 1.

13. A process according to claim 1, wherein the overhead cut from step 2 is etherified to transform isobutene into methyl tertiobutylether.

14. A process according to claim 1, wherein the separation of propylene in step 3 is conducted in a fractionation chain of steam cracking unit.

* * * * *